United States Patent
Shin et al.

(10) Patent No.: US 9,492,464 B2
(45) Date of Patent: Nov. 15, 2016

(54) COMPOSITION FOR PREVENTING OR TREATING SIDE EFFECT OF STEROID IN SUBJECT COMPRISING ACETYLSALICYLIC ACID AND USE THEREOF

(71) Applicant: Samsung Electronics Co., Ltd., Suwon-si, Gyeonggi-do (KR)

(72) Inventors: Euiseok Shin, Yongin-si (KR); Sangchul Park, Seongnam-si (KR); Sungchun Cho, Hwaseong-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/816,886

(22) Filed: Aug. 3, 2015

(65) Prior Publication Data

US 2016/0136185 A1 May 19, 2016

(30) Foreign Application Priority Data

Nov. 18, 2014 (KR) ........................ 10-2014-0160879

(51) Int. Cl.
*A61K 31/60* (2006.01)
*A61K 31/616* (2006.01)
*A61K 31/00* (2006.01)

(52) U.S. Cl.
CPC ............ *A61K 31/616* (2013.01); *A61K 31/00* (2013.01)

(58) Field of Classification Search
CPC .............................. A61K 31/616; A61K 31/60
USPC ....................................................... 514/165
See application file for complete search history.

(56) References Cited

U.S. PATENT DOCUMENTS

| 9,381,171 | B2 | 7/2016 | Cho et al. | |
| 2004/0138113 | A1 | 7/2004 | Kelly et al. | |
| 2009/0291928 | A1 | 11/2009 | Nishitani et al. | |
| 2010/0239690 | A1* | 9/2010 | Noda ................ | A61K 9/0014 424/693 |
| 2010/0297271 | A1 | 11/2010 | Mehal et al. | |
| 2011/0008413 | A1 | 1/2011 | Qiu et al. | |

OTHER PUBLICATIONS

Jones et al., Effects of a Novel Selective Androgen Receptor Modulator on Dexamethasone-Induced and Hypogonadism-Induced Muscle Atrophy, Endocrinology,Jul. 2010, 151(8), p. 3706-3719.*
Castillero et al., "PPARβ/d Regulates Glucocorticoid- and Sepsis-Induced FOXO1 Activation and Muscle Wasting", PLoS One, 8(3): 1-16 (e59726) (2013).
Galliher-Beckley et al., "Emerging Roles of Glucocorticoid Receptor Phosphorylation in Modulating Glucocorticoid Hormone Action in Health and Disease", *Life*, 61(10): 979-986 (2009).
Schakman et al., "Glucocorticoid-induced skeletal muscle atrophy", *The International Journal of Biochemistry and Cell Biology*, 45: 2163-2172, (2013).

* cited by examiner

*Primary Examiner* — T. Victor Oh
(74) *Attorney, Agent, or Firm* — Leydig, Voit & Mayer, Ltd.

(57) ABSTRACT

A method for preventing or treating side effects of glucocorticoid in a subject including administrating to a subject acetylsalicylic acid a pharmaceutically acceptable salt, solvate, or polymorph thereof, or a combination of at least two of the foregoing.

14 Claims, 2 Drawing Sheets

COMPOSITION FOR PREVENTING OR TREATING SIDE EFFECT OF STEROID IN SUBJECT COMPRISING ACETYLSALICYLIC ACID AND USE THEREOF

RELATED APPLICATION

This application claims the benefit of Korean Patent Application No. 10-2014-0160879, filed on Nov. 18, 2014, in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: 1,670 bytes ASCII (Text) file named "720404_ST25.TXT" created Jul. 2, 2015.

BACKGROUND

1. Field

The present disclosure relates to methods for preventing or treating side effects of steroids in a subject comprising administrating acetylsalicylic acid to the subject.

2. Description of the Related Art

Glucocorticoid formulations including dexamethasone have been clinically used as medications to treat various immune diseases and inflammations due to excellent immune-suppressive activities and anti-inflammatory effects thereof. However, dexamethasone may cause various side effects such as atrophy of tissues of muscle, brain, and skin, diabetes, and osteoporosis. Dexamethasone increases phosphorylation of a glucocorticoid hormone receptor in cells, thereby promoting transport of the glucocorticoid hormone receptor into a cell nucleus. The glucocorticoid hormone receptor transported into the cell nucleus increases expression of Forkhead box O (FOXO) protein, which is a transcription factor, thereby increasing expression of Atrogin-1 or MuRF-1 protein serving as an ubiquitin protein ligase. Atrogin-1 and MuRF-1 proteins induce ubiquitination of proteins essential for muscles, such as MyoD or myosin heavy chains, thereby promoting degradation of proteins of muscles and decreasing muscle mass. Thus, glucocorticoids such as dexamethasone may cause decreased muscle mass as a side effect.

The side effects caused by steroids such as glucocorticoids may be treated by administering antibacterial agents for infections, administering insulin and oral antidiabetic medications for diabetes, administering antiacids and H2 blocker for gastrointestinal tract symptoms, administering vitamin D or calcium for osteoporosis, administering ocular hypotensive agents for glaucoma, and administering antipsychotic drugs for mental disorders and state of depression.

However, there is still a need to develop methods of preventing or treating side effects in treatment of steroids such as glucocorticoids.

SUMMARY

Provided is a method of preventing or treating side effects of glucocorticoid treatment in a subject, the method comprising administering acetylsalicylic acid, a pharmaceutically acceptable salt, solvate, or polymorph thereof, or a combination of at least two of the foregoing into the subject.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
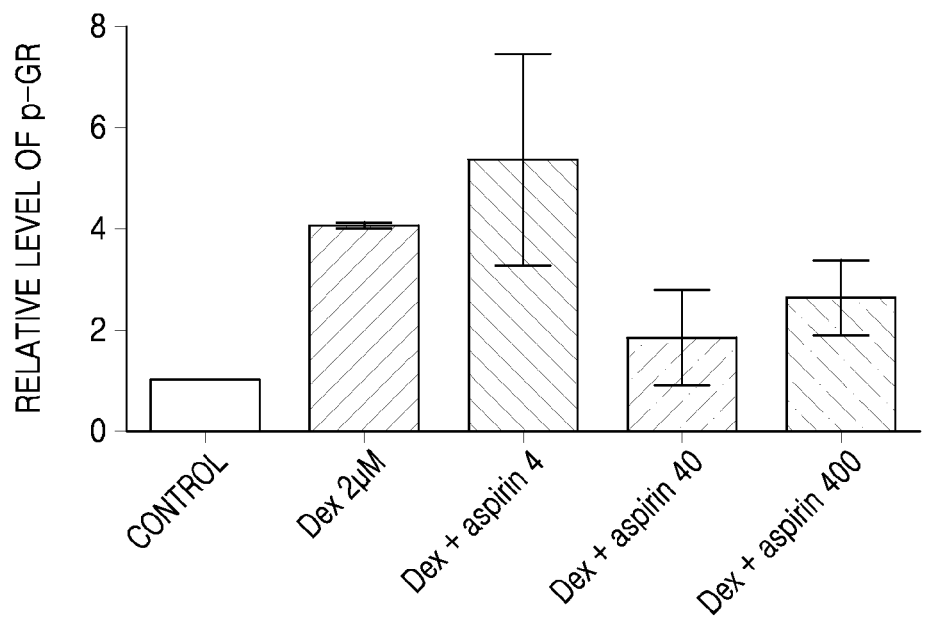
FIG. 1 is a graph illustrating relative levels of phosphorylated glucocorticoid receptor (pGR) obtained using an anti-pGR antibody when C2C12 myoblast cells are cultured in the presence of dexamethasone and/or acetylsalicylic acid (pGR: phosphorylated glucocorticoid receptor, GR: glucocorticoid receptor)

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

A composition for preventing or treating side effects of glucocorticoid in a subject according to an exemplary embodiment includes acetylsalicylic acid, a pharmaceutically acceptable salt, solvate, or polymorph thereof, or a combination of at least two of the foregoing.

Acetylsalicylic acid is 2-(acetyloxy)benzoic acid having a product name Aspirin. Acetylsalicylic acid is a derivative of salicylic acid often used as antifebriles, analgesics, non-steroidal anti-inflammatory drug (NSAID), or anti-rheumatism medicine. Acetylsalicylic acid has a structure represented by Formula I below. Acetylsalicylic acid is hydrolyzed into salicylic acid and acetic acid in water.

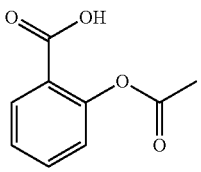

Formula I

Acetylsalicylic acid may be purchased from commercially available products, directly synthesized, or extracted, separated, or filtered from natural substances.

The pharmaceutically acceptable salt refers to a salt of a compound that does not cause significant irritation to an organism into which that salt is administered and does not damage the biological activity and physical properties of the compound. For example, the salt may be an inorganic acid salt, an organic acid salt, or a metal salt. Examples of the inorganic acid salt include hydrochloride, bromate, phosphate, sulfate, and disulfate. Examples of the organic acid salt include formate, acetate, propionate, lactate, oxalate, tartrate, malate, maleate, citrate, fumarate, besylate, camsylate, edisylate, trichloro acetate, trifluoro acetate, benzoate, gluconate, methane sulfonate, glycolate, succinate, 4-toluene sulfonate, galacturonate, embonate, glutamate, ethane sulfonate, benzene sulfonate, p-toluene sulfonate, or aspartate. Examples of the metal salt include calcium salt, sodium salt, magnesium salt, strontium salt, or potassium salt.

The solvate may be a compound produced by intermolecular attraction between a solute and a solvent. The solvate may be a hydrate.

The polymorph may be a substance present in more than one form or crystal structure.

The subject may be a mammal, such as human, cow, horse, pig, dog, sheep, goat, or cat.

The term "glucocorticoid (GC)" refers to a steroid hormone binding to a glucocorticoid receptor (GR or GCR) existing in most vertebrate cells. The glucocorticoid receptor that is also known as a nuclear receptor subfamily 3, group C, member 1 (NR3C1) is a receptor to which cortisol and other glucocorticoids bind. The glucocorticoid receptor may have GenBank Accession No. NP_000167 (human) and GenBank Accession No. NP_032199 (mouse) amino acid sequences. The glucocorticoid receptor may be encoded by GenBank Accession No. NM_000176 (human) and GenBank Accession No. NM_008173 (mouse) nucleotide sequences.

The glucocorticoid may include at least one selected from the group consisting of cortisol, hydrocortine, cortisone, prednisolone, methylprednisolone, triamcinolone, triamcinolone acetonide, paramethasone, dexamethasone, betamethasone, hexestrol, methimazole, fluocinonide, fluocinolone acetonide, fluorometholon, beclomethasone dipropionate, estriol, diflorasone diacetate, diflucortolone valerate, and difluprednate.

The side effects of excess glucocorticoid in a subject may be due to glucocorticoid treatment or other increase in an amount of glucocorticoid in the subject (e.g., Cushing's syndrome). The glucocorticoid treatment may involve administration of a glucocorticoid drug into the subject to prevent or treat diseases or symptoms of the subject.

Target diseases of glucocorticoid treatment may be diseases caused by an overactive immune system. Examples of the target diseases of glucocorticoid treatment include: endocrine diseases such as chronic adrenocortical insufficiency (e.g., primary, secondary, pituitary, and iatrogenic), acute adrenocortical insufficiency (e.g., adrenal crisis), adrenogenital syndrome, subacute thyroiditis, thyrotoxicosis [e.g., thyroidal (toxic) crisis], malignant exophthalmos associated with thyroidal diseases, and isolated ACTH deficiency; rheumatism diseases such as chronic rheumatoid arthritis, juvenile rheumatoid arthritis (including Still's diseases), rheumatic fever (including rheumatic pancarditis), and polymyalgia rheumatica; collagen diseases such as erythematosus (e.g., systemic and chronic discoidlupus), systemic vasculitis (including aortitis syndrome, periarteritis nodosa, polyarteritis, and Wegener granulomatosis), polymyositis (e.g., dermatomyositis), and scleroderma; renal diseases such as nephrosis and nephrosis syndrome; cardiac diseases such as congestive heart failure; allergic diseases such as bronchial asthma, asthmatic bronchitis (including childhood asthmatic bronchitis), allergy or intoxication due to medicament and other chemical substances (including drug eruption, toxic eruption), and serum sickness; severe infections such as severe infections (in combination with chemical therapy); blood diseases such as hemolytic anemia (with suspected immunity or immune mechanism), leukemia (e.g. acute leukemia, acute blastic crisis of chronic myelogenous leukemia, and chronic lymphatic leukemia) (including skin leukemia), agranulocytosis (e.g. primary and secondary), purpura (e.g. thrombocytopenic and nonthrombocytopenic), aplastic anemia, and hemorrhagic diathesis due to disorder of coagulation factor; gastrointestinal diseases such as localized enteritis and ulcerative colitis; severe consumption diseases, e.g., improvement of general condition (including terminal cancer or sprue) associated with severe consumption diseases; hepatic diseases such as fulminant hepatitis (including clinically severe cases), cholestatic acute hepatitis, chronic hepatitis (active type, recrudescent acute type, and cholestatic type) (limited to intractable one unresponsive to general treatments and with persistent noticeable abnormality in liver function), and cirrhosis (e.g., active type, condition accompanying intractable ascites, and condition accompanying cholestasis); lung diseases such as sarcoidosis (excluding condition with bilateral hilar adenopathy alone) and diffuse interstitial pneumonia (lung fibrosis) (including irradiation pneumonitis); tuberculous diseases (in combination with antitubercular agent) such as pulmonary tuberculosis (limited to miliary tuberculosis, severe tuberculosis), tuberculous meningitis, tuberculous pleurisy, peritoneal tuberculosis, and tuberculous pericarditis; neurological diseases such as encephalomyelitis (including encephalitis and myelitis) (to be used for a short period for primary encephalitis, when intracranial hypertensive symptom is observed and other drugs provide insufficient effect), peripheral neuritis (including Guillain-Barre syndrome), myotonia, myasthenia gravis, multiple sclerosis (including optic myelitis), chorea minor, facial paralysis, and spinal arachnoiditis; malignant tumor such as malignant lymphoma (e.g., lymphosarcomatosis, reticulosarcomatosis, Hodgkin's diseases, cutaneous reticulosis, and mycosis fungoides) and similar diseases (related diseases), eosinophilic granuloma, and recurrence metastasis of breast cancer; other medical diseases such as idiopathic hypoglycemia and unexplained fever; and infections such as SARS. In addition, the glucocorticoid treatment also includes treatment used for the purpose of suppressing rejection during organ transplantation such as liver transplantation and kidney transplantation.

Examples of the side effects of glucocorticoid treatments include: aggravation or induction of infections, concealment of symptoms, or impaired immunity; adrenocortical insufficiency; impaired glucose tolerance such as induction or aggravation of diabetes and elevation of blood glucose level; gastrointestinal tract ulcer, gastrointestinal hemorrhage, gastrointestinal perforation, and hemorrhagic pancreatitis; cramp and intracranial hypertension; mental disorders and state of depression; decreased bone metabolism such as osteoporosis (particularly, compression fracture of the spine); aseptic necrosis of bone head (femoral and humerus bone fractures); myopathy (loss of muscle strength accompanied by muscular atrophy, particularly, decreased muscle weight and loss of muscle strength of proximal muscle, and decreased muscle function) or a decrease of muscle mass, and body weight loss; glaucoma, high eye pressure, posterior capsular cataract, and thrombus (hypercoagulability); cardiac rupture due to myocardial infarction; aggravation of asthma attack; anaphylaxis due to injection; moon-shaped face and buffalo hump; elevation of blood pressure due to mineral effect; sodium-water retention (e.g., edema), body weight increase and hypokalemic alkalosis; development disorders in childhood; menstrual disorder; decrease in sperm motility and number; acne, hypertrichosis, hair loss, and deposit of pigment; dermal thinning, weakening, subcutaneous congestion, linear purpura, facial erythema, panniculitis, and cellulitis; hindrance of wound healing; hypersensitiveness (e.g., rash), itching, and hiccup; euphoria, insomnia, headache, and dizziness; dyshidrosis, excessive urination, and leukocytosis; fatty liver and nitrogen imbalance; GOT, GPT, and ALP increase; hyperlipidemia, hypercholesterolemia, and steroidnephropathy; nausea, vomiting, stomachache, heartburn, sense of abdominal fullness, dry mouth, diarrhea, and excessive appetite; retinal disorder or eyophthalmos due to central serous chorioretinopathy; muscular pain, arthritic pain, fever, and feeling of fatigue; atrophy in topical tissue due to muscle, intradermal or subcutaneous injection, depression, and body weight loss; thrombus, phlebitis, pain, swelling, and tenderness aggravation during intravenous injection; withdrawal syndrome; systemic symptom: fever, headache, inverse fatigue, generalized tiredness, feeling of weakness, and shock as systemic symptoms; anorexia, loss of appetite, nausea and vomiting, and diarrhea; nerve system-associated symptoms such as headache, anxiety, excitement/cramp, disturbance of consciousness, muscular pain, arthritic pain, and the like.

The side effects of glucocorticoid treatment may include at least one selected from the group consisting of muscular atrophy, decreased muscle function, muscular pain, arthritic pain, impaired glucose tolerance, loss of appetite, body weight loss, decreased bone metabolism, impaired immunity, and fatigability.

The side effects of glucocorticoid treatment may be caused by an increase in Atrogin-1 activity, an increase in activity of muscle ring-finger protein-1 (MuRF-1), or any combination thereof.

Atrogin-1 refers to F-box only protein 32 (FBXO32) that is a protein encoded by a FBXO32 gene in humans. The FBXO32 gene encodes about 40 amino acid motifs, members of an F-box protein family characterized by F-box. The F-box protein may constitute one of the four subunits of an ubiquitin protein ligase complex called SKP1-cullin-F-box (SCF), which function in phosphorylation-dependent ubiquitination. The Atrogin-1 activity is an ability of constituting an ubiquitin protein ligase complex or an activity of an ubiquitin protein ligase as the complex.

MuRF-1, also called E3 ubiquitin-protein ligase TRIM63, is an enzyme encoded by a TRIM63 gene in humans. The MuRF-1 activity may be an activity of the E3 ubiquitin-protein ligase. The MuRF-1 may have GenBank Accession No. NP_115977 (human) and GenBank Accession No. NP_001034137 (mouse) amino acid sequences. In addition, the MuRF-1 may be encoded by GenBank Accession No. NM_032588 (human) and GenBank Accession No. NM_001039048 (mouse) nucleotide sequences.

The term "increase in activity" refers to an increase in protein biosynthesis and an increase in specific activity of protein in comparison to the levels of protein biosynthesis and protein specific activities in a control (e.g., a cell or organism of the same type) to which acetylsalicylic acid has not been administered.

The composition may cause a decrease in Atrogin-1 activity, a decrease in MuRF-1 activity, or any combination thereof. The term "decrease in activity" refers to a decrease in protein biosynthesis or a decrease in specific activity of protein in comparison to the levels of protein biosynthesis and protein specific activities in a control (e.g., a cell or organism of the same type) to which acetylsalicylic acid has not been administered. In addition, the composition may reduce phosphorylation of a glucocorticoid receptor in comparison to levels of phosphorylation in a control (e.g., cell or organism of the same type) to which acetylsalicylic acid has not been administered.

The acetylsalicylic acid, the pharmaceutically acceptable salt, solvate, of polymorph thereof, or the combination of at least two of the foregoing thereof may reduce phosphorylation of the glucocorticoid receptor or migration of the phosphorylated glucocorticoid receptor into a nucleus in comparison to levels of phosphorylation or nuclear migration in a control (e.g., cell or organism of the same type) to which acetylsalicylic acid has not been administered.

The term "preventing" refers to inhibiting the occurrence of side effects of glucocorticoid treatment or occurrence of diseases caused thereby by administering the composition. The term "treating" refers to relieving or alleviating side effects of glucocorticoid treatment and diseases caused thereby by administering the composition.

The composition may include acetylsalicylic acid, a pharmaceutically acceptable salt, solvate, or polymorph thereof, or a combination of at least two of the foregoing in an effective amount. The effective amount may vary according to cells or subjects selected by those of ordinary skill in the art. The effective amount may be determined in accordance with seriousness of disease the side effects of glucocorticoid or diseases caused thereby, age, weight, health, gender, and sensitivity to drugs of patients, administration time, administration route, and excretion rate of the patient, treatment time period, ingredients including drugs combined with or simultaneously used with the composition according to an exemplary embodiment, and other ingredients well known in medicines. The effective amount may be in a range of about 10 mg to about 10 g, about 50 mg to about 9 g, about 100 mg to about 8 g, about 200 mg to about 7 g, about 300 mg to about 6 g, about 400 mg to about 5 g, about 500 mg to about 4 g, about 500 mg to about 3 g, about 500 mg to about 2 g, or about 500 mg to about 1 g per the composition.

The composition may be administered before, during, or after administering a glucocorticoid drug. In simultaneous administration, the composition and the glucocorticoid drug may be administered in the same formulation or simultaneously administered in separate formulations. The composition may be administered in a dose of about 0.001 mg/kg of body weight to about 100 mg/kg of body weight for adults once a day, multiple times a day, or once every few days.

The composition may be used to prevent or treat myopathy as the side effects of glucocorticoid treatments. The myopathy may include, for example, loss of muscle strength accompanied by muscular atrophy, particularly, decreased muscle weight or loss of muscle strength of proximal muscle, and decreased muscle function. Weight loss may include diseases or states accompanied by gradual loss of muscle mass. The loss of muscle may be caused by various factors such as genetic factors; age-related diseases such as hypertension, impaired glucose tolerance, diabetes, obesity, dyslipidemia, atherosclerosis, and cardiovascular diseases; chronic diseases such as cancer, autoimmune diseases, infectious diseases, acquired immunodeficiency syndrome (AIDS), chronic inflammatory diseases, arthritis, dystrophy, renal diseases, chronic obstructive pulmonary diseases, emphysema, rachitis, chronic lower back pain, peripheral nerve damage, central nervous system damage, and chemical damage; long-term fixed posture, impotent feeling such as fracture or trauma, and in bed recovery from surgery; and progressive decrease in skeletal muscle mass and muscle strength associated with aging. The myopathy may induce weakened physical conditions, thereby worsening health status or disabled body performance.

The composition may be a pharmaceutical composition or a functional food composition. The pharmaceutical composition or functional food composition may further include a pharmaceutically acceptable additive or edible additive. The composition may be formulated as unit formulations suitable for administration thereof into patients by using a method commonly used in the fields of pharmaceuticals and food.

The composition may be formulated in oral formulations or parenteral formulations. The oral formulations may be granules, powders, liquids, tablets, capsules, dry syrups, or any combination thereof. The parenteral formulations may be injections, or formulations for external use. Examples of the formulations for external use include cream, gel, ointment, skin emulsions, skin suspensions, transdermal patch, medication-containing bandage, lotions, or any combination thereof.

Provided is a method of preventing or treating side effects of glucocorticoid treatment in a subject including administering acetylsalicylic acid, a pharmaceutically acceptable salt, solvate, or polymorph thereof, or a combination of at least two of the foregoing into the subject.

The acetylsalicylic acid, the pharmaceutically acceptable salt, solvate, or polymorph thereof, the side effects of glucocorticoid treatment, the preventing, and the treating are as described herein.

The subject may have side effects caused by glucocorticoid. The subject may have side effects caused by glucocorticoid treatment or other increase in an amount of glucocorticoid in the subject.

The acetylsalicylic acid, the pharmaceutically acceptable salt, solvate, or polymorph thereof, or the combination of at least two of the foregoing may be administered before, during, or after administering a glucocorticoid drug.

The administration may be performed using any known method. The administration may be performed directly to the subject via oral, intravenous, intramuscular, transdermal, mucosal, intranasal, intratracheal, or subcutaneous administration. The administration may be systemic or local administration. The administration may be local administration into a region with side effects caused by glucocorticoid. The administration may be performed in a dose of about 0.001 mg/kg to about 100 mg/kg for adults once a day, multiple times a day, or once every few days for one day to one year.

According to the composition for preventing or treating side effects of glucocorticoid treatment in a subject including acetylsalicylic acid and use thereof according to an exemplary embodiment, the side effects of the subject caused by glucocorticoid treatment may be efficiently prevented or treated. It should be understood that the exemplary embodiments described herein should be considered in a descriptive sense only and not for purposes of limitation. Descriptions of features or aspects within each embodiment should typically be considered as available for other similar features or aspects in other embodiments.

Example 1

Identification of Inhibitory Effects of Aspirin on Side Effects of Glucocorticoid Treatment Effects of Aspirin on influence of glucocorticoid treatment on signal transmission in cells were identified. Thus, it was confirmed that administration of Aspirin inhibits side effects of glucocorticoid treatment. Dexamethasone was used as the glucocorticoid.

(1) Identification of Degree of Expression of Phosphorylated Glucocorticoid Receptor (pGR)

First, C2C12 cell lines (mouse gastrocnemius muscle, ATCC® CRL-1772™) were seeded in a 60 mm dish in 10% FBS/DMEM and incubated at 37° C. in a 5% $CO_2$ incubator. When the cells formed 70% confluent, the culture medium was replaced with 2% FBS/DMEM and the cells were cultured for 4 days to completely induce differentiation into muscle cells. C2C12 cell lines are mouse myoblast cell lines obtained by continuous culture of myoblast cells cultured from gastrocnemius muscle of C3H mice.

When C2C12 cells were completely differentiated into muscle cells, the culture medium was removed therefrom, and 4 ml of a fresh culture medium including 40 µM, 400 µM, or 4000 µM of Aspirin (Sigma Aldrich) was added thereto, and then the cells were cultured for 24 hours. 2 µM of dexamethasone (Sigma Aldrich) was added to the cultured cells and the cells were further cultured for 24 hours. A negative control group was not treated with acetylsalicylic acid and dexamethasone.

The culture medium was removed therefrom, and the cells were collected. Then, 500 µl of RIPA (20 mM Tris-HCl (pH 7.5), 150 mM NaCl, 1 mM $Na_2EDTA$, 1 mM EGTA, 1% NP-40, 1% (w/v) sodium deoxycholate, 2.5 mM sodium pyrophosphate, 1 mM beta-glycerophosphate, 1 mM $Na_3VO_4$, and 1 µg/ml leupeptin) lysis buffer was added thereto. The cells were lysed to obtain lysates. The lysates were subject to electrophoresis and immunoblotting using anti-phosphorylated glucocorticoid receptor (pGR) antibody (Abcam). FIG. 1 is a bar graph depicting the results obtained from the immunoblotting.

As illustrated in FIG. 1, dexamethasone induces phosphorylation of a dexamethasone receptor GR. As an amount of Aspirin increases, an amount of the glucocorticoid receptor GR phosphorylated by dexamethasone decreases. Thus, it was confirmed that Aspirin inhibits side effects caused by dexamethasone by inhibiting signal transduction induced by dexamethasone.

(2) Identification of Effects of Aspirin on Protection of Muscle Fiber

Diameters of muscle fibers according to addition of dexamethasone and/or Aspirin were measured to identify effects of Aspirin on protection of muscle fiber.

As described above with reference to Example 1(1), C2C12 cells were completely differentiated into muscle cells. After removing the culture medium, 4 ml of a fresh culture medium including 400 µM of Aspirin (Sigma Aldrich) was added thereto, and then the cells were cultured for 24 hours. 2 µM of dexamethasone (Sigma Aldrich) was added to the cultured cells, and the cells were cultured for 24 hours. A negative control group was not treated with acetylsalicylic acid and dexamethasone.

Figure 2:
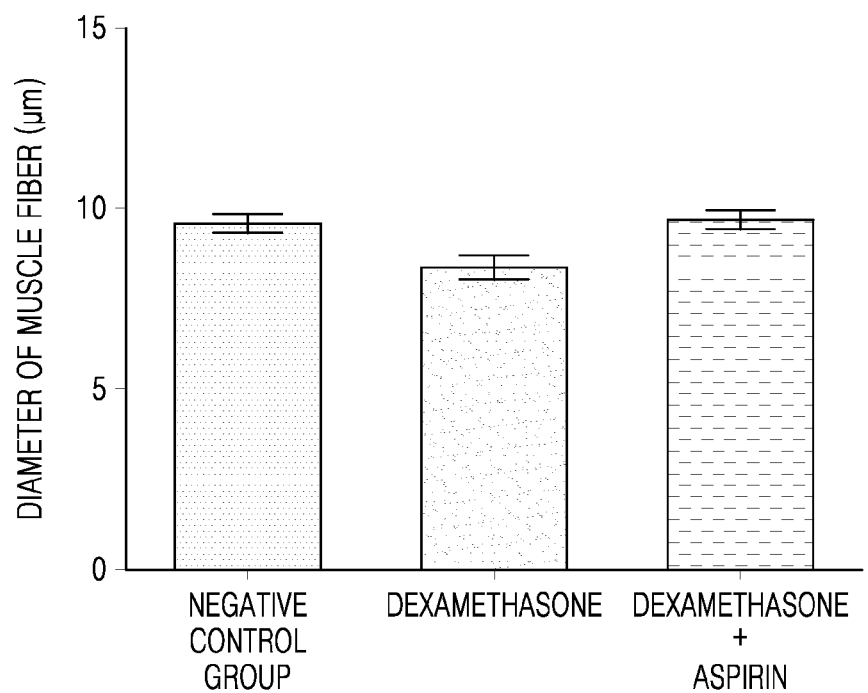
FIG. 2 is a graph illustrating diameters (μm) of muscle fiber measured when C2C12 myoblast cells are cultured in the presence of dexamethasone and/or acetylsalicylic acid.

A diameter (µm) of a muscle fiber was measured from a microscopic image (×400) of the muscle fiber of the cells, and the results are shown in FIG. 2.

As illustrated in FIG. 2, in a group treated with only dexamethasone without being treated with Aspirin, muscular atrophy was identified since the diameter of the muscle fiber was reduced. However, the diameter of the muscle fiber of a group pre-treated with Aspirin was similar to that of a control group. Thus, it was confirmed that Aspirin may inhibit loss of muscle mass, as a side effect of dexamethasone.

(3) Identification of Activity of Muscle Protease

Activities of muscle proteases induced by dexamethasone and/or Aspirin were identified.

As described above with reference to Example 1(2), C2C12 cells were completely differentiated into muscle cells, and 4 ml of a fresh culture medium including 400 μM of Aspirin (Sigma Aldrich) was added thereto, and then the cells were cultured for 24 hours. 2 μM of dexamethasone (Sigma Aldrich) was added to the cultured cells, and the cells were cultured for 24 hours. The culture medium was removed therefrom, and the cells were collected. A negative control group was not treated with acetylsalicylic acid and dexamethasone.

A Trizol reagent (Invitrogen) was added to the collected cells, and total RNA was separated therefrom according to manufacturer's protocols. Complementary DNA (cDNA) was synthesized from the separated total RNA by using a reverse transcriptase. Amounts of mRNA of Atrogin-1 and MuRF-1 were quantified using a real time PCR device (MyiQPCR instrument, BioRad) that is a device measuring SYBR Green. The results were normalized with respect to an amount of GAPDH mRNA. Amplification of Atrogin-1, MuRF-1, and GAPDH mRNA was performed an oligonucleotide set of SEQ ID NOS: 1 and 2, an oligonucleotide set of SEQ ID NOS: 3 and 4, and an oligonucleotide set of SEQ ID NOS: 5 and 6 as primers, respectively.

Figure 3A:
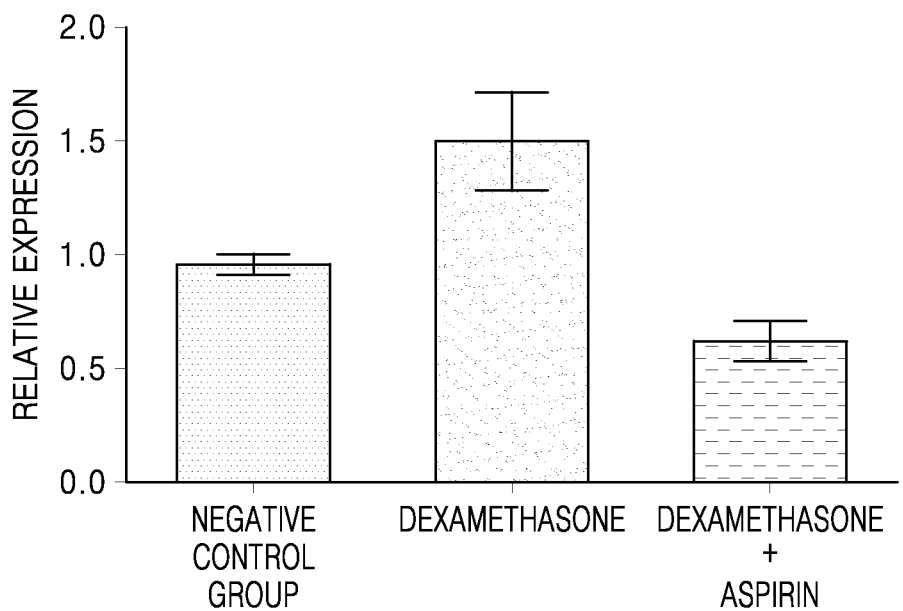
FIGS. 3A and 3B are graphs illustrating relative expression levels (arbitrary unit (AU)) of mRNA of Atrogin-1 (3A) and MURF-1 (3B) when C2C12 myoblast cells are cultured in the presence of dexamethasone and/or acetylsalicylic acid.
Figure 3B:
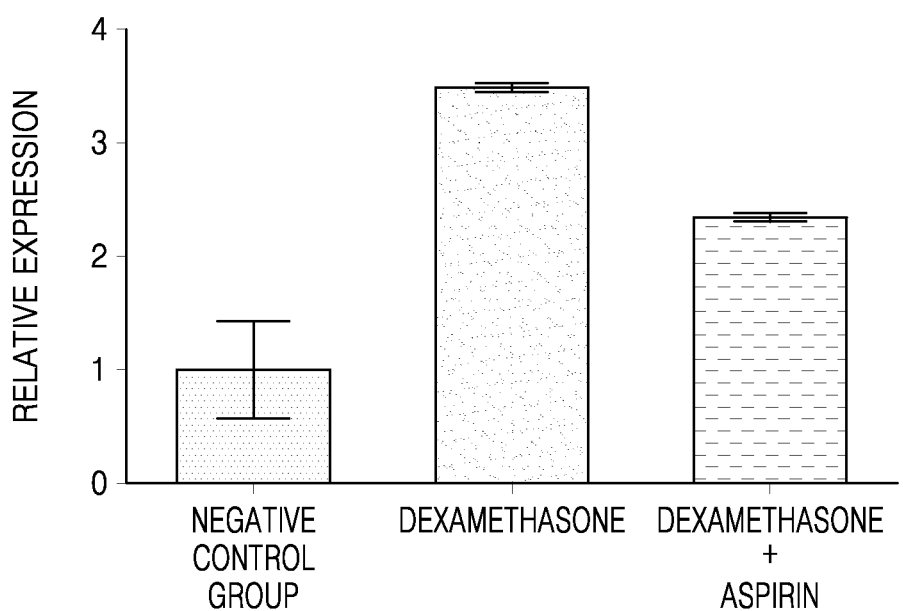

Values obtained via amplification were normalized by GAPDH gene, and relative expression levels of mRNA of Atrogin-1 and MURF-1 were quantified. The quantified relative expression levels (arbitrary unit (AU)) of mRNA of Atrogin-1 and MURF-1 are illustrated in FIGS. 3A and 3B, respectively, As illustrated in FIGS. 3A and 3B, while expression of Atrogin-1 and MuRF1 increased in cells treated with only dexamethasone, expression of mRNA of Atrogin-1 and MuRF1 did not increase in cells treated with both Aspirin and dexamethasone. Thus, it was confirmed that Aspirin inhibits expression of Atrogin-1 and MuRF1, which are proteases causing muscle loss, and thus degradation of muscle fiber caused by dexamethasone was inhibited, thereby preventing or treating muscle loss.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating a side effect of glucocorticoid treatment or other increase in glucocorticoid levels in a subject afflicted with such side effects, the method comprising administering acetylsalicylic acid or a pharmaceutically acceptable salt thereof to the subject.

2. The method of claim 1, wherein the side effect of glucocorticoid treatment is muscular atrophy, decreased muscle function, muscular pain, arthritic pain, impaired glucose tolerance, loss of appetite, body weight loss, decreased bone metabolism, impaired immunity, nephrotic syndrome, fatigability, or combination thereof.

3. The method of claim 1, wherein the side effect of glucocorticoid treatment is caused by an increase in Atrogin-1 activity, an increase in MuRF-1 activity, or a combination thereof.

4. The method of claim 1, wherein Atrogin-1 activity, MuRF-1 activity, phosphorylation of a glucocorticoid receptor (GR), or combination thereof is reduced in a subject by the administering of the acetylsalicylic acid.

5. The method of claim 1, wherein the at least one glucocorticoid comprises at least one selected from the group consisting of cortisol, hydrocortine, cortisone, prednisolone, methylprednisolone, triamcinolone, triamcinolone acetonide, paramethasone, dexamethasone, betamethasone, hexestrol, methimazole, fluocinonide, fluocinolone acetonide, fluorometholon, beclomethasone dipropionate, estriol, diflorasone diacetate, diflucortolone valerate, and difluprednate.

6. The method of claim 1, wherein the acetylsalicylic acid or pharmaceutically acceptable salt thereof, is administered in a dose in a range of about 0.001 mg/kg to about 100 mg/kg.

7. The method of claim 1, wherein the acetylsalicylic acid or pharmaceutically acceptable salt thereof is administered via oral, intravenous, intramuscular, transdermal, mucosal, intranasal, intratracheal, or subcutaneous administration.

8. The method of claim 1, wherein the acetylsalicylic acid or pharmaceutically acceptable salt thereof is administered once a day, multiple times a day, or once every three days.

9. A method for reducing Atrogin-1 or MuRF-1 activity levels in a subject treated with at least one glucocorticoid, comprising administering acetylsalicylic acid or a pharmaceutically acceptable salt thereof to the subject, wherein the Atrogin-1 and MuRF-1 activity levels are reduced in comparison to the activity levels in a control subject.

10. A method for reducing phosphorylation of the Glucocorticoid Receptor (GR) in a subject treated with at least one glucocorticoid, comprising administering acetylsalicylic acid or a pharmaceutically acceptable salt thereof to the subject, wherein the phosphorylation level of GR is reduced in comparison to the phosphorylation levels of GR in a control subject.

11. The method of claim 1, wherein the acetylsalicylic acid is administered via oral, intravenous, intramuscular, or subcutaneous administration.

12. The method of claim 1, wherein the acetylsalicylic acid is administered via the oral route in the form of a tablet consisting essentially of acetylsalicylic acid.

13. A method of glucocorticoid treatment with reduced side effects, the method consisting of administering to a subject in need of glucocorticoid treatment a glucocorticoid and acetylsalicylic acid or a pharmaceutically acceptable salt thereof.

14. The method of claim 13, wherein the glucocorticoid and acetylsalicylic acid are administered as a single composition.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Synthetic primer for mouse atrogin-1/MAFbx

<400> SEQUENCE: 1
cacattctct cctggaaggg c                                          21

<210> SEQ ID NO 2
<211> LENGTH: 21
<212> TYPE: DNA
<213> ORGANISM: Artificial Sequence
<220> FEATURE:
<223> OTHER INFORMATION: Synthetic primer for mouse atrogin-1/MAFbx
```

```
<400> SEQUENCE: 2
ttgataaagt cttgagggga a                                              21

<210> SEQ ID NO 3
<211> LENGTH: 20
<212> TYPE: DNA
<213> ORGANISM: Artificial Sequence
<220> FEATURE:
<223> OTHER INFORMATION: Synthetic primer for mouse MuRF-1

<400> SEQUENCE: 3
acgagaagaa gagcgagctg                                                20

<210> SEQ ID NO 4
<211> LENGTH: 22
<212> TYPE: DNA
<213> ORGANISM: Artificial Sequence
<220> FEATURE:
<223> OTHER INFORMATION: Synthetic primer for mouse MuRF-1

<400> SEQUENCE: 4
cttggcactt gagagaggaa gg                                             22

<210> SEQ ID NO 5
<211> LENGTH: 20
<212> TYPE: DNA
<213> ORGANISM: Artificial Sequence
<220> FEATURE:
<223> OTHER INFORMATION: Synthetic primer for mouse GAPDH

<400> SEQUENCE: 5
catggccttc cgtgttccta                                                20

<210> SEQ ID NO 6
<211> LENGTH: 17
<212> TYPE: DNA
<213> ORGANISM: Artificial Sequence
<220> FEATURE:
<223> OTHER INFORMATION: Synthetic primer for mouse GAPDH

<400> SEQUENCE: 6
gcggcacgtc agatcca                                                   17
```